United States Patent
Smith et al.

(10) Patent No.: US 6,585,694 B1
(45) Date of Patent: Jul. 1, 2003

(54) KNOB-CONTROLLED ENDOSCOPIC NEEDLE DEVICE

(75) Inventors: Kevin W. Smith, Coral Gables, FL (US); Juergen A. Kortenbach, Miami Springs, FL (US); Thomas O. Bales, Coral Gables, FL (US)

(73) Assignee: Syntheon, LLC, Miami, FL (US)

( * ) Notice: Subject to any disclaimer, the term of this patent is extended or adjusted under 35 U.S.C. 154(b) by 109 days.

(21) Appl. No.: 09/656,599

(22) Filed: Sep. 7, 2000

(51) Int. Cl.[7] .......................... A61M 5/00; A61M 5/178; A61B 17/10
(52) U.S. Cl. .................. 604/181; 604/158; 604/164.01; 604/164.12; 604/165.02; 128/750; 606/142
(58) Field of Search ....................... 604/164.01, 164.12, 604/165.02, 158, 181, 264; 128/750; 606/142

(56) References Cited

U.S. PATENT DOCUMENTS

| | | | |
|---|---|---|---|
| 4,763,667 A | | 8/1988 | Manzo ....................... 128/750 |
| 4,940,458 A | * | 7/1990 | Cohn ......................... 600/561 |
| 5,279,570 A | * | 1/1994 | Dombrowski et al. .. 604/164.01 |
| 5,322,510 A | * | 6/1994 | Lindner et al. ............. 239/423 |
| 5,324,306 A | * | 6/1994 | Makower et al. ........... 606/213 |
| 5,380,292 A | | 1/1995 | Wilson ........................ 604/164 |
| 5,425,718 A | * | 6/1995 | Tay et al. ................... 604/158 |
| 5,584,812 A | * | 12/1996 | Martin ................... 604/164.08 |
| 5,766,184 A | * | 6/1998 | Matsuno et al. ............... 604/15 |
| 5,785,689 A | * | 7/1998 | de Toledo et al. .......... 604/158 |
| 5,843,017 A | * | 12/1998 | Yoon .......................... 600/564 |
| 5,957,893 A | * | 9/1999 | Luther et al. ........... 604/164.01 |
| 6,102,920 A | * | 8/2000 | Sullivan et al. ............. 606/147 |
| 6,126,633 A | * | 10/2000 | Kaji et al. ............. 604/164.01 |
| 6,134,467 A | * | 10/2000 | Ouchi .................... 604/164.01 |
| 6,206,849 B1 | * | 3/2001 | Martin et al. ............... 604/264 |
| 6,258,064 B1 | * | 7/2001 | Smith et al. ........... 604/164.12 |

* cited by examiner

Primary Examiner—William C. Doerrler
Assistant Examiner—Filip Zec
(74) Attorney, Agent, or Firm—Gordon & Jacobson, P.C.

(57) ABSTRACT

An endoscopic needle device includes an inner fluid conduit, an outer sheath extending over the length of the conduit, a longitudinally stiff wire extending through the conduit, and a needle fixedly attached to the distal end of the conduit. The distal end of the wire is coupled to one or both of the needle and the distal end of the conduit. The needle includes a proximal opening such that the hollow of the needle is in fluid communication with a lumen of conduit. A proximal handle includes a stationary member and a movable member longitudinally movable relative to the stationary member. The proximal end of the outer sheath is coupled to the stationary member, and the stationary member includes structure to mount the handle to a port of an endoscope. The movable member includes a passageway, and the proximal end of the conduit is coupled to the distal end of the movable member, and a port is provided at the proximal end of the movable member. A syringe may be coupled to the port and operated to inject a fluid which travels through the passageway, the lumen of the conduit, and the needle. In addition, the proximal end of the wire is coupled to the movable member. The handle assembly also includes a knob rotatably coupled to the stationary member, wherein rotation of the knob results in reciprocal movement of the movable member relative to the stationary, and consequently the needle relative to the distal end of the outer sheath.

15 Claims, 4 Drawing Sheets

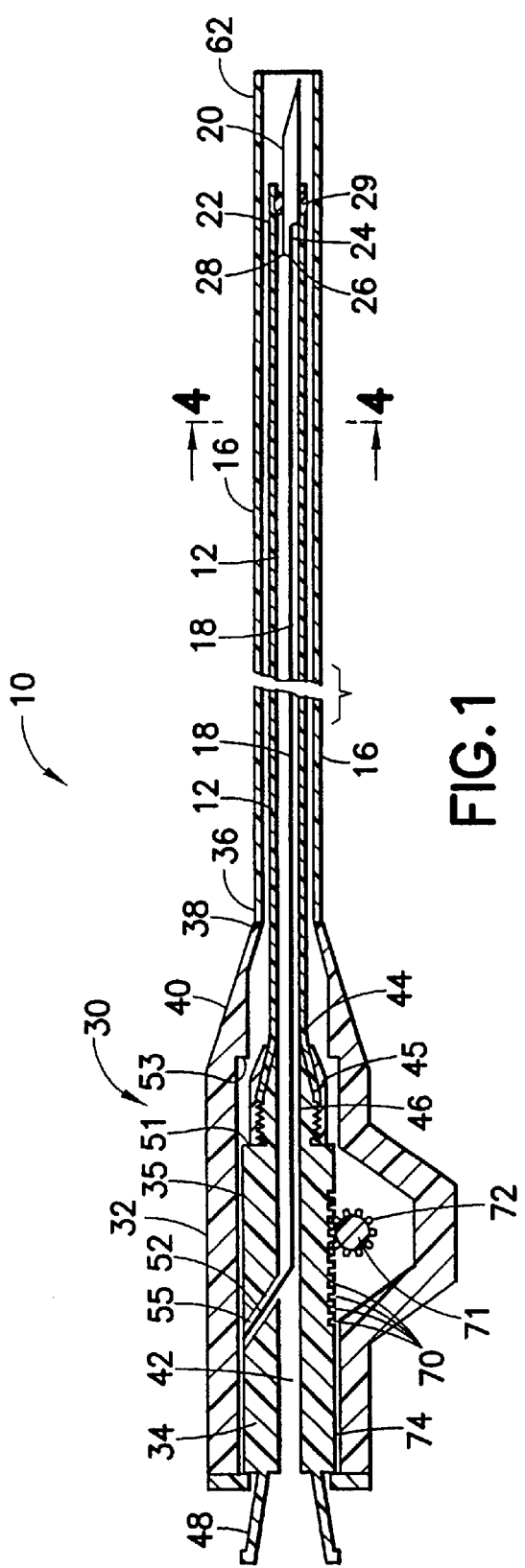
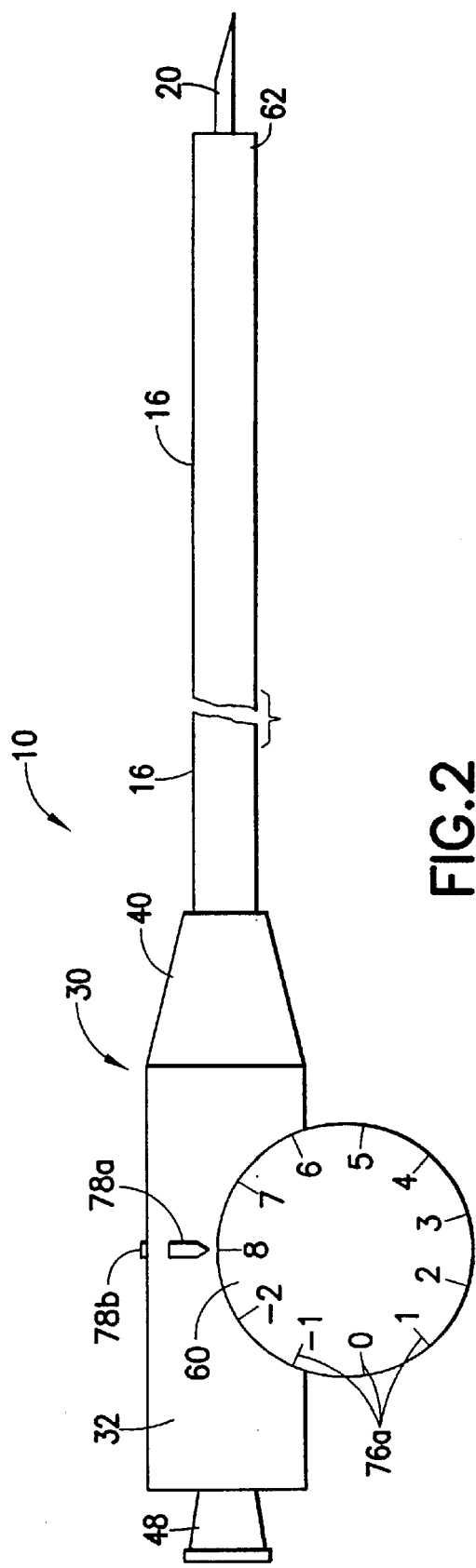

KNOB-CONTROLLED ENDOSCOPIC NEEDLE DEVICE

BACKGROUND OF THE INVENTION

1. Field of the Invention

This invention relates broadly to endoscopic instruments. More particularly, this invention relates to endoscopic injection needle devices.

2. State of the Art

An endoscopic injection needle device is inserted through a lumen of a flexible endoscope to inject fluids under endoscopic visualization in body structures such as the esophagus, the stomach, and the colon. For example, during a colonic polypectomy, it is customary to inject saline solution into the tissue surrounding and underlying a polyp in order to raise the polyp to facilitate excision of the polyp by means of an endoscopic forceps or snare. Visible dyes and radiological contrast dyes are sometimes injected to mark the location of areas explored endoscopically so that the structures can be located during subsequent procedures. Additionally, sclerosing agents are sometimes injected into vascular structures, such as esophageal varicoceles, in order to cause clotting and to necrose the tissue so that it can be resorbed by the body.

Typically, an injection needle device consists of a flexible inner tubing (or fluid conduit), usually made of polytetrafluoroethylene (PTFE), surrounded by a loose-fitting outer jacket made of PTFE, fluorinated ethylene propylene (FEP), or similar flexible plastic, a handle assembly at the proximal ends of the inner tubing and outer jacket for relative axial movement thereof, and a needle attached to the distal end of the inner tubing.

In practice, a physician grips the outer jacket of the injection needle device with one hand to introduce it through a sealing port on the endoscope handle which communicates with the working channel of the endoscope and to position the distal end of the device proximate the desired tissue at the distal end of the endoscope. With his or her other hand, the physician holds the proximal handle of the endoscope so that the steering knobs on the endoscope handle can be manipulated while viewing the endoscopic image. The handle assembly of the endoscopic needle device is held and manipulated by an assistant, according to the oral commands of the physician. The assistant moves one component of the handle assembly relative to the other to move the inner tubing axially relative to the outer jacket, thus retracting the needle into the outer jacket or extending it beyond the distal tip of the outer jacket. Once the needle is in position, the assistant then injects a fluid or medicament into the tissue by means of a syringe attached to the handle assembly of the device.

The amount of penetration of the needle into the tissue is not easily controlled by either the physician or the assistant. The depth of penetration of the needle is limited only by the fact that the fluid conduit (or the connector joining the needle point to the fluid conduit) which is larger in diameter than the needle, abuts the tissue. In an alternative procedural method, the physician pushes the jacket up against the tissue, and then the physician orders the assistant to fully advance the needle. In this manner, there is no visualization or degree of control to the penetration of the needle point, except as limited by the abutment of the fluid conduit or connector against the tissue. If the physician determines that a different amount of needle penetration is desired, another device with a needle point of a different length must be used.

While it is customary for a physician to standardize his practice with a needle of a certain penetration length, it sometimes is necessary to inject more superficially, to reduce the possibility of penetrating the tissue structure, or more deeply, to reach a plane of dissection to separate layers of tissue. Therefore, it is necessary to stock several injection needle devices in each gastroenterology suite, each device having a needle with a different length to accommodate the needs of the physician.

A few prior art devices have been built which allow the assistant to control the depth of needle projection beyond the distal end of the jacket, but these devices are imprecise and awkward. For example, the devices described in U.S. Pat. No. 5,380,292 to Wilson and U.S. Pat. No. 4,763,667 to Manzo attempt to achieve a measure of adjustability of the needle projection by utilizing an adjustable stop on the handle assembly of the device. The Wilson and Manzo devices do not have a calibrated control mechanism, and there is no way for the assistant to accurately adjust the depth of needle penetration while the device is in place in the endoscope, because such would require visualization of the needle point and measurement of its projection beyond the distal end of the jacket while turning an adjustment nut. Rather, the Wilson and Manzo devices simply provide a manner by which the device can be prepared prior to use for a specific amount of needle projection. Unfortunately, even the adjustable stop is of limited value, because the design of these prior art devices is such that the length of needle point projection beyond the jacket is highly variable despite the stop. In fact, the position of the needle is strongly influenced by the shape of the endoscope and by forces acting on the needle point. Depending on the degree to which the endoscope is flexed to negotiate the anatomy of the patient, the length of needle projection of most prior art devices is variable because of the various possible positions of the fluid conduit tubing within the loose-fitting outer jacket of the device. Thus, as the device is flexed, the needle point moves relative to the distal end of the jacket. Also, such designs which use a flexible plastic tube for the fluid conduit, are not amenable to precise control of the needle projection, because their needles will retract to some degree, typically a few millimeters, when forced against tissue. That is, the fluid conduit compresses. Thus, these devices do not teach a practicable means of controlling the length of needle projection while the device is being used.

U.S. Pat. No. 5,766,184 to Matsuno et al. describes another needle device having an outer tubular sheath, an inner tubular member extending through the outer tubular sheath and longitudinally and axially rotatably movable relative thereto, a shaft extending through the inner tubular member and coupled to the needle, a needle at the distal end of the inner tubular member, and a handle assembly including a knob which permits axial rotation of the shaft, and therefore the inner tubular member and needle, relative to the sheath. The needle and the distal end of the outer sheath are threadably connected. This threaded connection permits helical rotation of the inner tubular member relative to the outer tubular sheath to cause longitudinal movement of the needle relative to the distal end of the outer tubular sheath. Fluid is injectable through the inner tubular member and the needle into the patient. However, the device has severe drawbacks. It is generally desirable that the pitch of the threads be sufficiently small to permit the fine and precise adjustment of the extension of the needle, e.g., movement of the needle to within a half millimeter. Such fine adjustment requires that the pitch of the thread in the connection preferably be no more than a half millimeter. Yet, this requires that the inner tubular member be rotated a very large number of times relative to the outer tubular member in order to move the needle the required distance. For example, at a pitch of a quarter millimeter, the inner tubular member and outer tubular sheath would need to be completely rotated thirteen times relative to each other in order to effectuate a 6.5 millimeter movement of the needle. Such device operation is impractical for two reasons. First, it is impractical for the physician or assistant to keep count of how many times he or she has rotated the knob which causes the inner tubular member to rotate relative to the outer tubular member. However, keeping count is required as there is no other means by which to determine how far the needle has been extended. As such, absent reliance on the physician's or assistant's memory as to how may times the inner tubular member and outer tubular sheath have been rotated relative to each other, it is not possible to determine from the proximal end of the instrument the extension of the needle from the distal end of the instrument. Second, even if the physician or assistant could accurately keep count of the number of rotations, such repetitive rotational movement is uncomfortable, resulting in hand strain. Therefore, this needle device is undesirable to both the physician and the assistant. In addition, the patent fails to adequately describe a handle assembly which can correctly accommodate axial movement of the shaft and inner tubular member relative to the outer sheath as the needle is helically advanced and retracted.

SUMMARY OF THE INVENTION

It is therefore an object of the invention to provide an endoscopic needle device having a proximal handle assembly which accurately indicates the extension of the needle from the distal end of the device.

It is another object of the invention to provide an endoscopic needle device which may be conveniently and comfortably operated.

It is a further object of the invention to provide an endoscopic needle device in which the needle is precisely adjustable to deliver different depths of penetration of the needle point while the device is in use.

It is also an object of the invention to provide an endoscopic needle device which precisely controls the position of the needle relative to the distal end of the jacket.

It is an additional object of the invention to provide an endoscopic needle device in which extension of the needle is not affected by such factors as compressibility of the tubular components.

In accord with these objects, which will be discussed in detail below, an endoscopic needle device is provided which includes an inner fluid conduit, an outer sheath extending over the length of the conduit, an elongate longitudinally stiff wire or other element extending through the conduit, and a needle fixedly attached to the distal end of the conduit. The distal end of the wire is coupled to one or both of the needle and the distal end of the conduit. The needle includes a proximal opening such that the hollow of the needle is in fluid communication with a lumen of conduit. A proximal handle assembly includes a stationary member and a movable member longitudinally movable relative to the stationary member. The proximal end of the outer sheath is coupled to the stationary member, and the stationary member includes structure to mount the handle to a port of an endoscope. The movable member includes a passageway, and the proximal end of the conduit is coupled to the distal end of the movable member, and a port, e.g., a luer connector, is provided at the proximal end of the movable member. A syringe may be coupled to the port and operated to inject a fluid (injectate) which travels through the passageway, the lumen of the conduit, and the needle. In addition, the proximal end of the wire is coupled to the movable member. The handle assembly also includes a shaft rotatably coupled to the stationary member, wherein rotation of a knob coupled to the shaft results in reciprocatory (proximal-distal and distal-proximal) movement of the movable member relative to the stationary member, and consequently the needle relative to the distal end of the outer sheath.

According to a first embodiment of the invention, the movable member includes a rack, and the knob is provided with a pinion which engages the rack. Rotation of the knob relative to the stationary member causes the pinion to rotate relative to the movable member, and thus causes reciprocatory movement of the movable member relative to the stationary member which operates to move the position of the needle relative to the distal end of the endoscope. Precise movement is facilitated by the longitudinally stiff wire which extends through the fluid lumen, of the conduit. The wire counters the compressive force to which the conduit is subject when the movable member is moved distally relative to the stationary member. The knob and the stationary member are provided with indicia which indicate the movement of the needle.

According to a second embodiment of the invention, substantially similar to the first embodiment, the conduit is provided with at least two lumina, one for the injectate and the other for the wire. As such, the wire is not in contact with the injectate.

According to a third embodiment of the invention, a gear reduction assembly includes a change gear including two gears of different diameters on a common shaft. The smaller diameter gear engages the rack and the larger diameter gear engages the pinion. The gear reduction assembly permits larger gear teeth to be used on the pinion and rack, thereby facilitating manufacture and assembly of the device.

According to a fourth embodiment of the invention, a rolling band mechanism is utilized to reciprocate the movable member relative to the stationary member. In the rolling band mechanism, a band is wrapped one turn around a shaft attached to the knob, and the ends of the band are held taught at or adjacent ends of the movable member. The band and the shaft frictionally interfere. Rotation of the shaft by the knob causes the shaft to engage the band and results in reciprocal movement of the movable member relative to the stationary member.

According to a fifth embodiment of the invention, the movable member includes a portion provided with a rack, and a screw provided with threads engages the rack. Rotation of a knob portion of the screw causes reciprocatory movement of the movable member relative to the stationary member.

In each embodiment, the position of the knob relative to the housing provides an indication of the extension of the needle. In addition, the longitudinal stiffness of the wire ensures that proximal movement of the conduit relative to the sheath results in like movement of the distal end of the conduit relative to the sheath. As such, the injection needle device of the invention permits controllable movement of the needle such that the needle can be easily, reliably, and precisely advanced and withdrawn.

Additional objects and advantages of the invention will become apparent to those skilled in the art upon reference to the detailed description taken in conjunction with the provided figures.

BRIEF DESCRIPTION OF THE DRAWINGS

FIG. 1 is a broken longitudinal section of an endoscopic injection needle device according to a first embodiment of the invention, shown with the needle withdrawn;

FIG. 2 is a broken side elevation view of the endoscopic injection needle device shown with the needle extended;

DETAILED DESCRIPTION OF THE PREFERRED EMBODIMENTS

Figure 3:
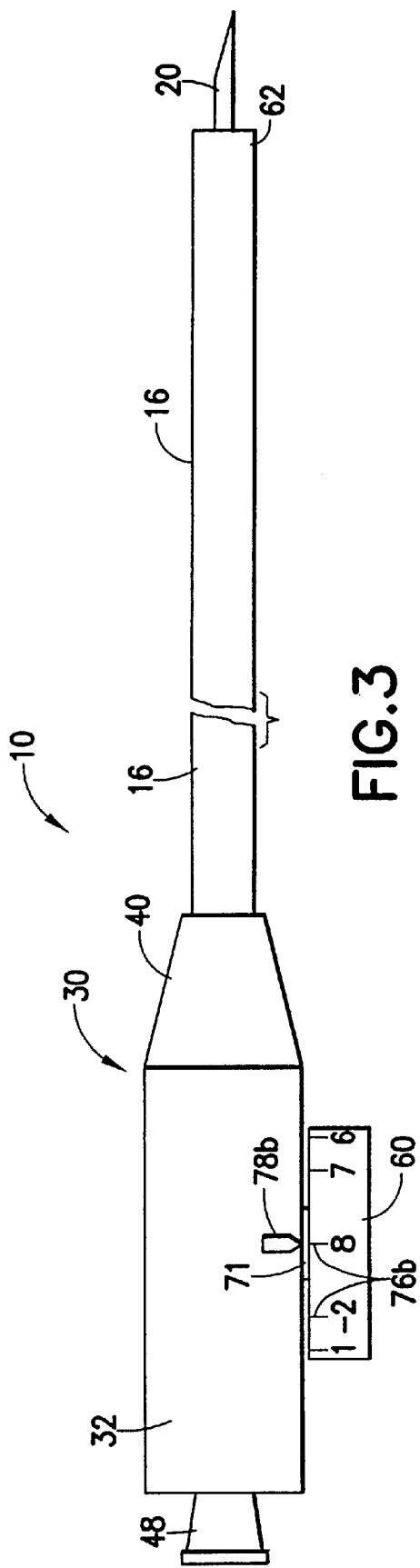
FIG. 3 is a broken top view of the endoscopic injection needle device shown with the needle extended.

Turning now to FIGS. 1 through 4, a first embodiment of an endoscopic injection needle device 10 includes an inner flexible tubular fluid conduit 12 having a lumen 14, an outer sheath 16 extending over the length of the conduit, a wire 18 extending through the lumen 14 of the conduit, and a needle 20 fixedly attached to the distal end 22 of the conduit 12. The needle 20 includes a proximal opening 24 such that the hollow of the needle is in fluid communication with a lumen 14 of conduit. The distal end 26 of the wire 18 is coupled, e.g., by crimping or bonding, to one or both of the needle 20 and the distal end 22 of the conduit.

The fluid conduit 12 is preferably a length of PTFE tubing, and provides flexibility, sufficient strength to resist internal fluid pressure, and inertness to all known injectates. By way of example, the conduit 12 may be an extruded tubing with an outside diameter of 0.078 inches and an inner diameter of 0.055 inches. The sheath 16 is preferably a length of PTFE, FEP, or similar flexible plastic and has inner and outer diameters sized to be movable over the conduit and within a channel of an endoscope, respectively.

The shaft 18 is preferably a high strength, straightened (camber-free) stainless steel wire which extends continuously from the distal end of the conduit 12 to a handle assembly 30, as discussed below. The camber-free shaft 18 has a high elastic limit, and may be bent with the needle device through a tortuous path without permanent deformation. By way of example, the shaft 14 may be 304V spring-temper wire of 325,000 psi UTS and 0.017 inch diameter.

The needle 20 is preferably made from stainless steel tubing, preferably 25 gauge, and preferably has a standard needle point grind at its distal end. According to one preferred embodiment, the proximal end of the needle is cut away to form a tab 28, to which the distal end 26 of the wire 18 is secured. In addition, the needle is attached to and closes off the distal end of the fluid conduit with a crimp band 29, by bonding, or in any other manner, so long as a fluid passageway is provided between the lumen 14 and the needle 20.

A proximal handle assembly 30 includes a stationary housing 32 and a movable member 34 which reciprocates relative to and preferably within a longitudinal bore 35 of the housing 32. The proximal end 36 of the outer sheath 16 is coupled, e.g., bonded, to a distal end 38 of the housing 32. In addition, the housing 32 includes a mount 40, e.g., a resilient frustoconical portion, which is adapted to stably mount the housing 32 to a port of an endoscope (not shown). The movable member 34 includes a passageway 42, and the proximal end 44 of the conduit 12 is coupled, e.g., via a flare nut connection 45, to the distal end 46 of the movable member 34, and a port 48, e.g., a female luer connection, is provided at the proximal end 50 of the movable member 34. A shoulder 51 on the movable member 34, and a stop 53 on the housing 32 limit the distal movement of the movable member within the housing. A syringe (not shown) may be coupled to the port 48 and operated to inject a fluid (injectate) which travels through the passageway 42, the lumen 14 of the conduit 12, and the needle 20. In addition, the proximal end 52 of the wire 18 is secured in a bore 55 in the movable member 34. The handle assembly 30 also includes a shaft 71 rotatably coupled to the housing 32. As described below, rotation of the shaft 71 results in reciprocal movement of the movable member 34 relative to the housing 32, and consequently the needle 20 relative to the distal end 62 of the outer sheath 16.

According to the first embodiment of the invention, the movable member 32 includes a toothed rack 70, and the shaft 71 is provided with a manually rotatable knob 60 and a toothed pinion 72 which engages the rack 70. The rack 70 is preferably provided at a lower surface 74 of the movable member to facilitate an ergonomic placement and operation of the knob 60. Rotation of the knob 60 relative to the housing 32 causes the pinion 72 to rotate relative to the movable member 34, and thus causes reciprocatory movement of the movable member 34 relative to the housing 32. This reciprocatory movement operates to longitudinally move the position of the needle 20 relative to the distal end of the sheath 16. Preferably a total of at least ten millimeters of movement (e.g., two millimeters of retraction into the sheath 16, and eight millimeters of projection beyond the distal end 62 of the sheath) is enabled. For example, if the desired amount of reciprocatory motion is approximately ten millimeters and this motion is to be effected by a near full turn of the knob 60, e.g., 300°, the pitch circumference of the pinion 72 is equal to approximately twelve millimeters (360/300 times 10 mm). Thus, the pitch diameter of the pinion 72 is approximately 3.8 millimeters.

Precise movement is facilitated by the longitudinally stiff wire 18. That is, the wire 18 prevents the compressive forces which exist when the movable member 34 is moved distally relative to the housing 32 from compressing the conduit 12. The knob 60 and the housing 32 are preferably each provided with indicia 76a, 76b, 78a, 78b which indicate the position of the needle 20 relative to the distal end 62 of the sheath 16.

Figure 5:
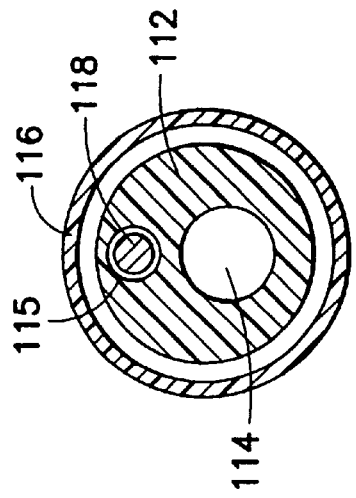
FIG. 5 is a view similar to FIG. 4 of a second embodiment of the invention.
Figure 4:
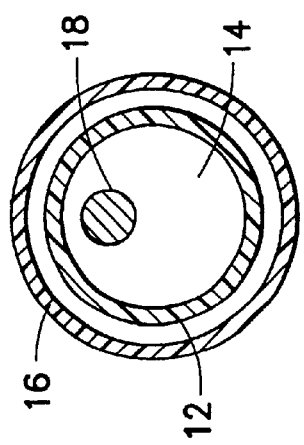
FIG. 4 is an enlarged cross-section across line 4—4 in FIG. 1.

Referring to FIG. 5, according to a second embodiment of the invention, substantially similar to the first embodiment 10 (with like parts having numbers incremented by 100), the conduit 112 within the sheath 116 includes first and second lumina 114, 115. The first lumen 114 is in fluid communication with the port connector 48 (FIG. 1) and the second lumen 115 receives the wire 118 therethrough. The connections (not shown) at the distal and proximal ends of the conduit 112 can be made with crimp bands of a malleable material, such as stainless steel. The wire 118 in the second lumen 115 is not in contact with the fluid injected through the first lumen 114 of the conduit 112.

Figure 6:
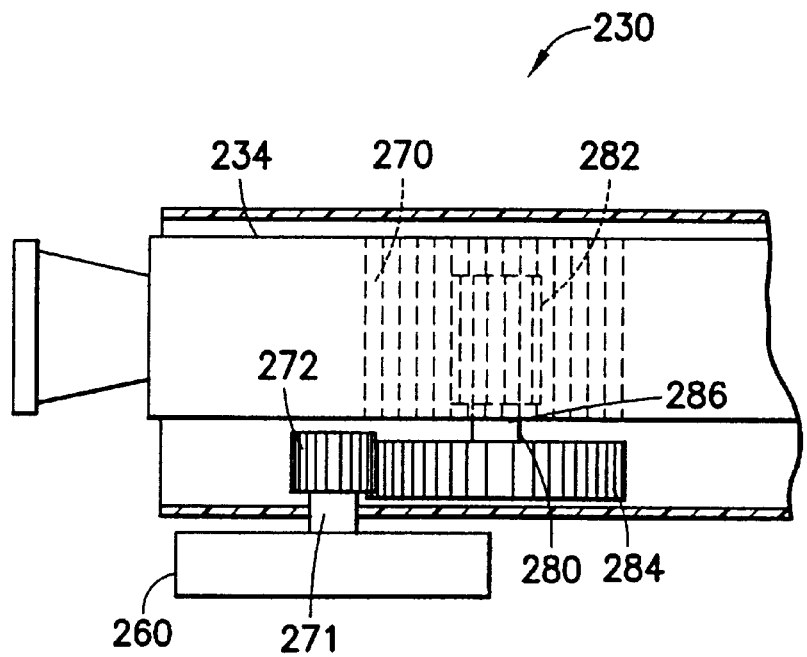
FIG. 6 is a top view of a broken partial section of a handle assembly according to a third embodiment of the injection needle device of the invention.

Turning now to FIG. 6, according to a third embodiment of the invention, substantially similar to the first embodiment 10 (with like parts having numbers incremented by 200), a change gear 280 is provided between the pinion 272 of the shaft 271 and the rack 270 on the movable member 234. The change gear 280 includes first and second gears 282, 284 of different diameter on a common shaft 286. The smaller diameter first gear 282 engages the rack 270 and the larger diameter second gear 284 engages the pinion 272. The change gear 280 is used to facilitate manufacture of the handle assembly 230. That is, in the first embodiment, the size of the pinion 72 is relatively small. This small pitch, though possible to manufacture, is difficult to manufacture, as it requires very small gear teeth and a high degree of precision in the production and location of the toothed components. The change gear 280 is used to implement a gear reduction, e.g., 2:1 or 4:1, such that the diameters of the small gears may be increased to a more practical size for manufacture and assembly.

Figure 7:
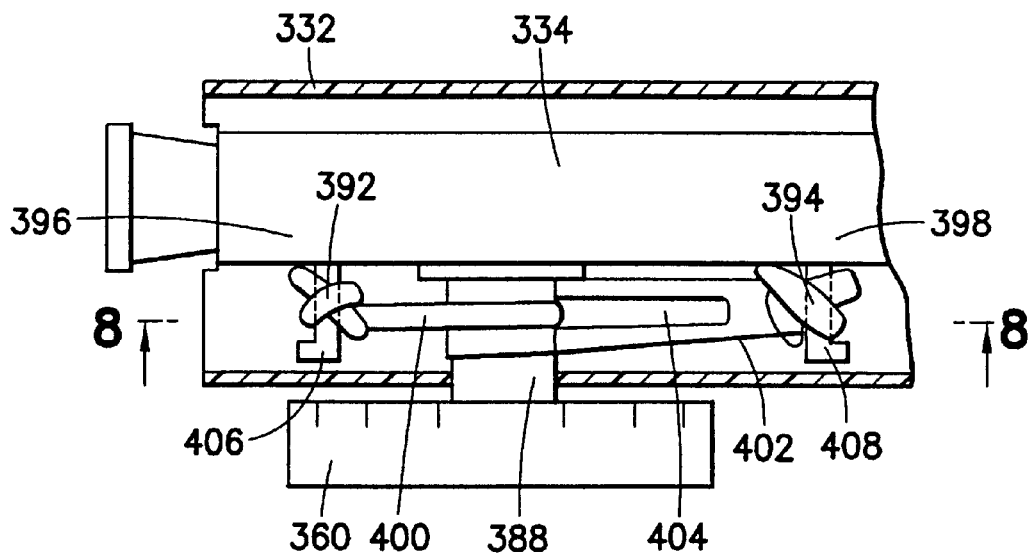
FIG. 7 is a top view of a broken partial section of a handle assembly according to a fourth embodiment of the injection needle device of the invention.
Figure 8:
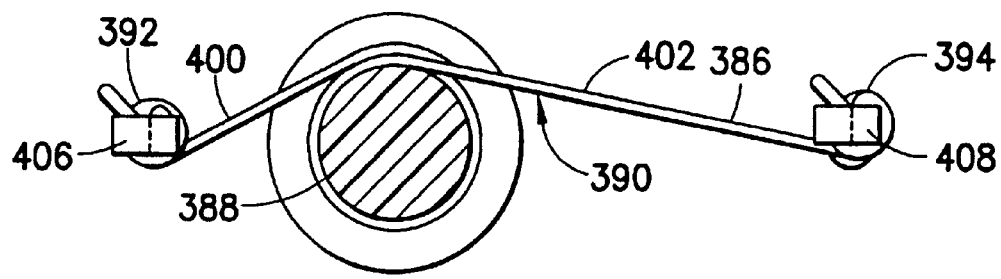
FIG. 8 is a side view across line 8—8 in FIG. 7.

Referring now to FIGS. 7 and 8, a fourth embodiment of the invention, substantially similar to the first embodiment, (with like parts having numbers incremented by 300), is shown. According to the fourth embodiment, the movable member 334 is reciprocated relative to the housing 332 via a rolling band 386 coupled to the movable member 334 and a rotatable shaft 388 frictionally engaging the band. The rolling band 386 is a band of flexible material preferably having a high friction surface 390. The band 386 is wrapped preferably one turn around the shaft 388, and the ends 392, 394 of the band are held taught between relatively proximal and distal portions 396, 398, respectively, of the movable member 334. The band 386 preferably has a first, e.g., proximal, portion 400 of a first width, and a second, e.g., distal, portion 402 of a second width greater than the first width. The second portion 402 includes a slot 404, and the first portion 400 is passed through the slot 404 when the band 386 is wrapped around the shaft 388, thereby eliminating the need to helically wrap the band about the shaft. Nevertheless, according to an alternate non-preferred configuration, the band 386 may be helically wrapped about the shaft 388, eliminating the need for a band with a varying width and a slot. The proximal end 392 of the band 386 is secured to the proximal portion 396, e.g., via a hook 406, while the distal end 394 of the band is secured to the distal portion 398, e.g., a hook 408. The band 386 and the shaft 388 frictionally interfere such that rotation of the shaft by the knob 360 causes the band to move relative to the shaft. This movement results in reciprocal movement of the movable member relative to the stationary member.

The band 386 may be either elastic, e.g., rubber, or substantially inelastic. In addition, the surface 390 of the band 386 and the shaft 388 may be provided with interengaging teeth or other structure to result in positive engagement or high friction between the band and shaft.

Figure 9:
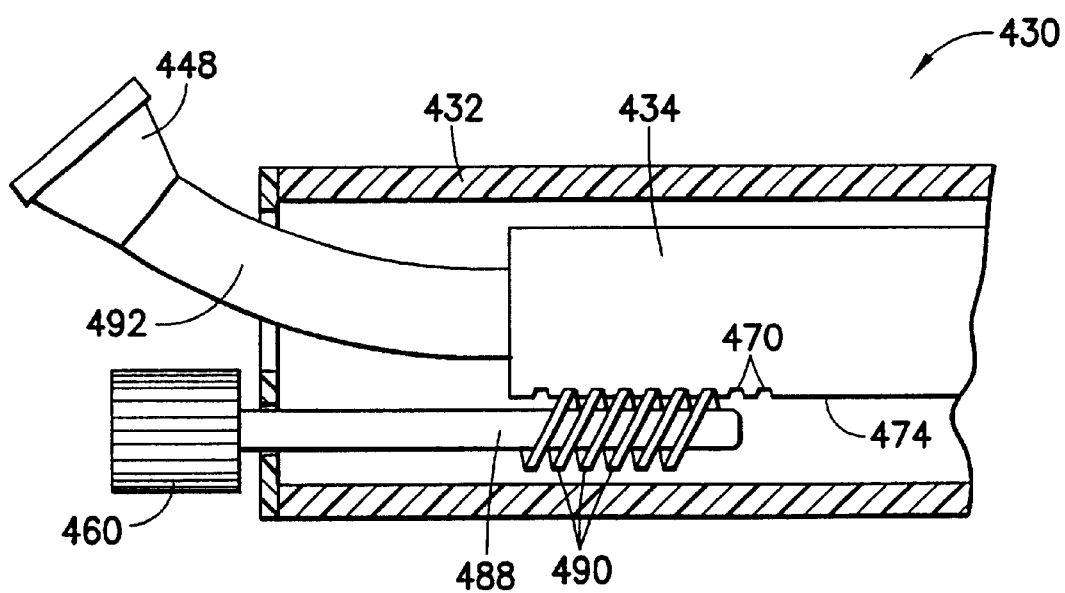
FIG. 9 is a broken partial section side view of a proximal handle assembly according to a fifth embodiment of the invention.

Referring now to FIG. 9, a fifth embodiment of the invention, substantially similar to the first embodiment (with like parts having numbers incremented by 400), is shown. The movable member 434 of the handle 430 includes a portion, e.g., the lower surface, 474, which is provided with a rack 470. A screw 488 including a proximal control knob 460 is rotatably coupled to the housing 432. The screw 488 includes a plurality of helical threads 490 which engage the rack 470. The screw 488 is oriented parallel to the axis of reciprocating movement between the movable member 434 and the housing 432. Rotation of the knob 460 causes the rotation of the threads 490 which results in linear movement of the movable member relative to the housing. Furthermore, the port 448 may be coupled to the movable member 434 via a flexible tube 492, such that the port 448 may be moved into a location which does not obstruct the knob 460.

In each embodiment, the position of the knob relative to the housing, and the respective indicia thereon, preferably provides an indication of the extension of the needle. In addition, the longitudinal stiffness of the wire ensures that proximal movement of the conduit relative to the sheath results in like movement of the distal end of the conduit relative to the sheath.

As a result, a single operator of the device, whether physician or assistant, can rotate the control knob relative to the housing and cause precise longitudinal movement and extension of the needle relative to the distal end of the sheath. The distance of longitudinal movement is indicated at the handle assembly by the indicia. The endoscopic injection needle device precisely controls advancement of a needle to within a fraction of a millimeter. In addition, the same operator or a second operator can also inject fluid from within a syringe coupled to the port through the conduit and needle and into the tissue where the extended needle is located.

There have been described and illustrated herein embodiments of an endoscopic needle injection device. While particular embodiments of the invention have been described, it is not intended that the invention be limited thereto, as it is intended that the invention be as broad in scope as the art will allow and that the specification be read likewise. Thus, while particular materials have been disclosed, other suitable materials may be used. In addition, while a particular mount has been shown which is adapted to mount the device to a port of an endoscope, other mounts, such as a threaded connector, can also be used. Also, while the movable member is described as being within a closed bore of the housing, the movable member may be provided in an open bore, i.e., a groove or channel. Furthermore, while a particular change gear has been disclosed, it will be understood that gears with other numbers of gear teeth, and other relative ratios, can be used. Moreover, while a band wrapped one turn is disclosed, it will be appreciated that the band can be wrapped more than one turn about the shaft. In addition, while the wider portion of the band is shown as being located relatively distally, the wider and narrower portions of the band can be oppositely located. Also, while the relative position of the needle relative to the sheath is indicated by the alignment of indicia, it will be appreciated that their relative positions may be indicated through a mechanical indicator operated by the gear assembly. Also, while a metal wire has been disclosed, it will be appreciated that non-metal elements which are longitudinally stiff, may also be used. In addition, while axial needle movement of between eight and twelve millimeters is preferred, the device may be adapted to permit greater or lesser needle movement. It will therefore be appreciated by those skilled in the art that yet other modifications could be made to the provided invention without deviating from its spirit and scope as claimed.

What is claimed is:

1. A needle injection device having a longitudinal axis, said device for injecting an injectate into tissue, comprising:

a) a flexible conduit having at least one lumen and proximal and distal ends;

b) a flexible sheath having proximal and distal ends and extending over and longitudinally movable relative to said conduit;

c) a needle coupled to said distal end of said conduit and having a bore in fluid communication with said at least one lumen of said conduit;
d) a longitudinally stiff element having proximal and distal ends and extending through said at least one lumen of said conduit, said distal end of said longitudinally stiff element coupled to at least one of said needle and said distal end of said conduit; and
e) a handle assembly including,
   i) a stationary member coupled to said proximal end of said sheath,
   ii) a movable member coupled said proximal ends of longitudinally stiff element and said conduit, said movable member including a port adapted to receive an injectate, and a passageway, wherein said port, said passageway, and said at least one lumen are in fluid communication, and
   iii) actuation means for non-rotationally reciprocating said movable member relative to said stationary member such that said distal ends of said longitudinally stiff element and said conduit are moved longitudinally relative to said distal end of said sheath, wherein said actuation means is adapted to reciprocate said movable member relative to said stationary member upon receiving a rotational input, said actuation means includes a shaft rotatably coupled to said stationary member, said shaft including a manually operable control knob rotatable about an axis perpendicular to said longitudinal axis of said device, and said movable member is provided with means for engaging said shaft such that rotation of said shaft causes said movable member to reciprocate relative to said stationary member.

2. A needle injection device according to claim 1, wherein:
said longitudinally stiff element is made from a metal or metal-alloy wire.

3. A needle injection device according to claim 1, wherein:
said at least one lumen comprises first and second lumina, said needle being in fluid communication with said first lumen and said longitudinally stiff element extending through said second lumen.

4. A needle injection device according to claim 1, wherein:
at most one complete rotation of said knob is required to move said needle between a completely advanced position and a completely withdrawn position.

5. A needle injection device according to claim 1, wherein:
said knob and said stationary member are provided with cooperating indicators to indicate a position of said needle relative to said distal end of said sheath.

6. A needle injection device for injecting an injectate into tissue, comprising:
a) a flexible conduit having at least one lumen and proximal and distal ends;
b) a flexible sheath having proximal and distal ends and extending over and longitudinally movable relative to said conduit;
c) a needle coupled to said distal end of said conduit and having a bore in fluid communication with said at least one lumen of said conduit;
d) a longitudinally stiff element having proximal and distal ends and extending through said at least one luen of said conduit, said distal end of said longitudinally stiff element coupled to at least one of said needle and said distal end of said conduit; and
e) a handle assembly including,
   i) a stationary member coupled to said proximal end of said sheath,
   ii) a movable member coupled said proximal ends of longitudinally stiff element and said conduit, said movable member including a port adapted to receive an injectate, and a passageway, wherein said port, said passageway, and said at least one lumen are in fluid communication, and
   iii) actuation means for non-rotationally reciprocating said movable member relative to said stationary member such that said distal ends of said longitudinally stiff element and said conduit are moved longitudinally relative to said distal end of said sheath, said actuation means including a band held taught between relatively proximal and distal portions of said movable member, said band being wrapped about a circumference of said shaft rotatably coupled to said stationary member,
   wherein rotation of said shaft about said stationary member causes said movable member to reciprocate relative to said stationary member.

7. A needle injection device according to claim 6, wherein:
said band includes a first portion having a first width, a second portion having a second width greater than said first portion and a longitudinal slot in said second portion, said first portion extending at least partially through said slot.

8. A needle injection device according to claim 6, wherein:
said band is helically wrapped about said shaft.

9. A needle injection device for injecting an injectate into tissue, comprising:
a) a flexible conduit having at least one lumen and proximal and distal ends;
b) a flexible sheath having proximal and distal ends and extending over and longitudinally movable relative to said conduit;
c) a needle coupled to said distal end of said conduit and having a bore in fluid communication with said at least one lumen of said conduit;
d) a longitudinally stiff element having proximal and distal ends and extending through said at least one lumen of said conduit, said distal end of said longitudinally stiff element coupled to at least one of said needle and said distal end of said conduit; and
e) a handle assembly including,
   i) a stationary member coupled to said proximal end of said sheath,
   ii) a movable member coupled said proximal ends of longitudinally stiff element and said conduit, said movable member including a port adapted to receive an injectate, and a passageway, wherein said port, said passageway, and said at least one lumen are in fluid communication, and
   iii) actuation means for non-rotationally reciprocating said movable member relative to said stationary member such that said distal ends of said longitudinally stiff element and said conduit are moved longitudinally relative to said distal end of said sheath, said actuation means including a screw having at least one thread, said screw having a longitudinal axis parallel to a longitudinal axis of said device, and said movable member includes a rack portion engaged by said at least one thread, wherein rotation of said screw causes said movable member to reciprocate relative to said stationary member.

10. A needle injection device according to claim 1, wherein:

said handle assembly includes means for indicating an axial position of said needle relative to said distal end of said sheath.

11. A needle injection device for injecting an injectate into tissue, comprising:
 a) a flexible conduit having at least one lumen and proximal and distal ends;
 b) a flexible sheath having proximal and distal ends and extending over and longitudinally movable relative to said conduit;
 c) a needle coupled to said distal end of said conduit and having a bore in fluid communication with said at least one lumen of said conduit;
 d) a longitudinally stiff element having proximal and distal ends and extending through said at least one lumen of said conduit, said distal end of said longitudinally stiff element coupled to at least one of said needle and said distal end of said conduit; and
 e) a handle assembly including,
  i) a stationary member coupled to said proximal end of said sheath, said stationary member including a bore,
  ii) a movable member reciprocative within said bore and coupled to said proximal ends of longitudinally stiff element and said conduit, said movable member including a port adapted to receive an injectate, and a passageway, wherein said port, said passageway, and said at least one lumen are in fluid communication,
  iii) means for reciprocating said movable member relative to said stationary member, said means for reciprocating including at least one of gears, threads, and friction bands, and
  iv) an indicator which indicates an axial position of said needle relative to said distal end of said sheath.

12. A needle injection device for injecting an injectate into tissue, comprising:
 a) a flexible conduit having at least one lumen and proximal and distal ends;
 b) a flexible sheath having proximal and distal ends and extending over and longitudinally movable relative to said conduit;
 c) a needle coupled to said distal end of said conduit and having a bore in fluid communication with said at least one lumen of said conduit;
 d) a longitudinally stiff element having proximal and distal ends and extending through said at least one lumen of said conduit, said distal end of said longitudinally stiff element coupled to at least one of said needle and said distal end of said conduit; and
 e) a handle assembly including,
  i) a stationary member coupled to said proximal end of said sheath,
  ii) a movable member coupled said proximal ends of said longitudinally stiff element and said conduit, said movable member including a rack portion and a port adapted to receive the injectate, and a passageway, wherein said port, said passageway, and said at least one lumen are in fluid communication,
  iii) a shaft including a pinion and a control knob, said shaft rotatably coupled to said stationary member, and
  iv) a gear element including a first gear and a second gear, said first gear coupled to said pinion and said second gear coupled to said rack, wherein said first and second gears are of different sizes.

13. A needle injection device according to claim 12, wherein:

said first gear is smaller than said second gear.

14. A needle injection device according to claim 12, wherein:

said handle assembly indicates an axial position of said needle relative to said distal end of said sheath.

15. A needle injection device for injecting an injectate into tissue, comprising:
 a) a flexible conduit having a first lumen and a second lumen and proximal and distal ends;
 b) a flexible sheath having proximal and distal ends and extending over and longitudinally movable relative to said conduit;
 c) a needle coupled to said distal end of said conduit and having a bore in fluid communication with said first lumen of said conduit;
 d) a longitudinally stiff element having proximal and distal ends and extending through said second lumen of said conduit, said distal end of said longitudinally stiff element coupled to at least one of said needle and said distal end of said conduit; and
 e) a handle assembly including,
  i) a stationary member coupled to said proximal end of said sheath,
  ii) a movable member coupled said proximal ends of longitudinally stiff element and said conduit, said movable member including a port adapted to receive the injectate, and a passageway, wherein said port, said passageway, and said first lumen are in fluid communication, and
  iii) actuation means for reciprocating said movable member relative to said stationary member such that said distal ends of said longitudinally stiff element and said conduit are moved longitudinally relative to said distal end of said sheath.

* * * * *